(12) United States Patent
Mori et al.

(10) Patent No.: US 7,495,768 B2
(45) Date of Patent: Feb. 24, 2009

(54) ANALYSIS METHOD AND APPARATUS AND ANALYSIS UNIT

(75) Inventors: Nobufumi Mori, Kanagawa-ken (JP); Katsumi Hayashi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 165 days.

(21) Appl. No.: 11/077,159

(22) Filed: Mar. 11, 2005

(65) Prior Publication Data
US 2005/0200853 A1    Sep. 15, 2005

(30) Foreign Application Priority Data
Mar. 11, 2004   (JP) .............................. 2004-069177

(51) Int. Cl.
*G01N 21/55* (2006.01)
(52) U.S. Cl. ..................................... 356/445
(58) Field of Classification Search ................. 356/445; 422/82.05
See application file for complete search history.

(56) References Cited

U.S. PATENT DOCUMENTS

| 6,104,484 | A | * | 8/2000 | Nagata et al. | ............... | 356/246 |
| 6,597,456 | B2 | | 7/2003 | Kubo et al. | | |
| 6,753,188 | B2 | * | 6/2004 | Perkins et al. | .............. | 356/445 |
| 6,992,770 | B2 | | 1/2006 | Naya | | |
| 2003/0075697 | A1 | | 4/2003 | Ohtsuka et al. | | |
| 2003/0113231 | A1 | * | 6/2003 | Karube et al. | ............. | 422/82.05 |
| 2003/0156292 | A1 | * | 8/2003 | Naya | .......................... | 356/445 |
| 2003/0206291 | A1 | * | 11/2003 | Byrne et al. | ................. | 356/136 |

FOREIGN PATENT DOCUMENTS

| EP | 1 324 019 A1 | 7/2003 |
| JP | 4-501462 A | 3/1992 |
| JP | 6-167443 A | 6/1994 |
| JP | 9-257806 A | 10/1997 |
| JP | 2001-255267 A | 9/2001 |

(Continued)

OTHER PUBLICATIONS

Schuck P. et al., "Determination of Binding Constants by Equilibrium Titration with Circulating Sample in a Surface Plasmon Resonance Biosensor", Analytical Biochemistry, vol. 265, 1998, pp. 79-91, XP002333786.

Okamoto, "Surface Refracto-Sensor using Evanescent Waves: Principles and Instrumentations," Spectrum Researches, vol. 47, No. 1, (1997), pp. 19-28.

(Continued)

*Primary Examiner*—Gregory J Toatley, Jr.
*Assistant Examiner*—Juan D Valentin
(74) *Attorney, Agent, or Firm*—Sughrue Mion, PLLC

(57) ABSTRACT

An analysis chip comprises a thin film layer, which is formed on a dielectric material block and has two different regions. A flow path unit comprising a supply path for supplying a sample onto the thin film layer and a discharging path for discharging the sample is releasably loaded into the analysis chip. A light beam is irradiated to a first interface between one region of the thin film layer and the dielectric material block, and a second interface between the other region of the thin film layer and the dielectric material block, in a parallel manner. Refractive index information with regard to a substance to be analyzed, which is located on the thin film layer, is acquired from intensities of the light beam totally reflected from the first interface and the light beam totally reflected from the second interface.

17 Claims, 9 Drawing Sheets

FOREIGN PATENT DOCUMENTS

| | | | |
|---|---|---|---|
| JP | 2002-131319 | A | 5/2002 |
| JP | 2002-357544 | A | 12/2002 |
| JP | 2003-302399 | A | 10/2003 |
| WO | WO 90/05295 | A1 | 5/1990 |
| WO | WO 03/002985 | A1 | 1/2003 |

OTHER PUBLICATIONS

Noort, et al, "Porous Gold in Surface Plasmon Resonance Measurement," Eurosensors XIII, (1999) pp. 585-588.

Nikitin et al, "Surface Plasmon Resonance Interferometry for Micro-Array Biosensing", Eurosensors XIII, (1999) pp. 235-238.

\* cited by examiner

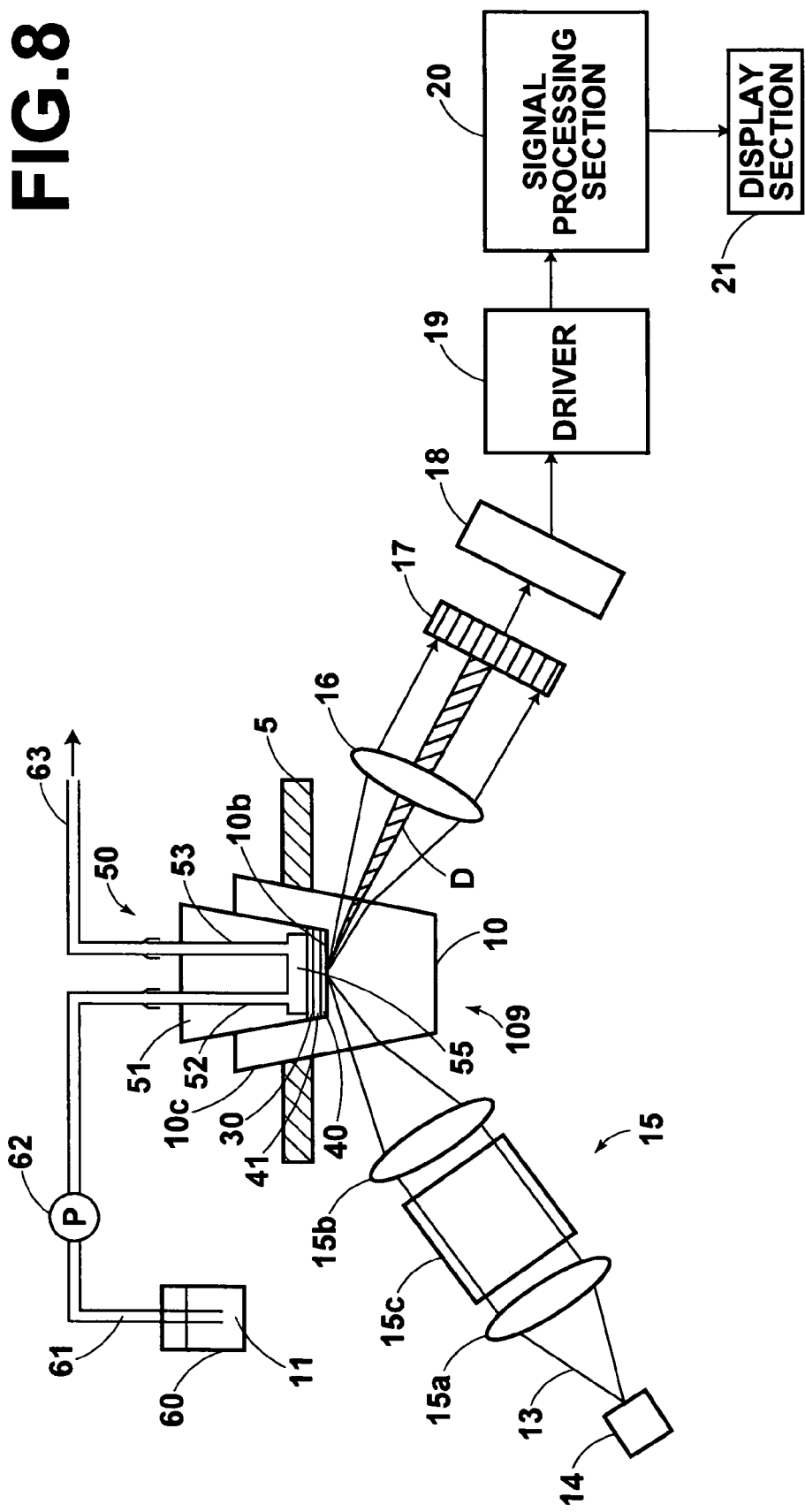

ANALYSIS METHOD AND APPARATUS AND ANALYSIS UNIT

BACKGROUND OF THE INVENTION

1. Field of the Invention

This invention relates to an analysis method and apparatus, wherein a light beam is totally reflected from an interface between a thin film layer, which is in contact with a sample, and a dielectric material block, an evanescent wave is thus caused to occur, and an alteration occurring with an intensity of the totally reflected light beam due to the occurrence of the evanescent wave is measured for an analysis of the sample. This invention also relates to an analysis unit for use in the analysis method and apparatus.

2. Description of the Related Art

As analysis apparatuses utilizing evanescent waves, surface plasmon sensors have heretofore been known. In metals, free electrons vibrate collectively, and a compression wave referred to as a plasma wave is thereby produced. The compression wave occurring on the metal surface and having been quantized is referred to as the surface plasmon. With the surface plasmon sensors, characteristics of samples are analyzed by the utilization of a phenomenon, in which the surface plasmon is excited by a light wave. Various types of surface plasmon sensors have heretofore been proposed. As one of well known surface plasmon sensors, a surface plasmon sensor utilizing a system referred to as the Kretschman arrangement may be mentioned. The surface plasmon sensor utilizing the system referred to as the Kretschman arrangement is described in, for example, Japanese Unexamined Patent Publication No. 6(1994)-167443.

Basically, the surface plasmon sensor utilizing the system referred to as the Kretschman arrangement comprises (i) a dielectric material block having, for example, a prism-like shape, (ii) a metal film, which is formed on one surface of the dielectric material block and is brought into contact with a sample, (iii) a light source for producing a light beam, (iv) an optical system for irradiating the light beam to the dielectric material block at various different incidence angles such that a total reflection condition may be obtained at an interface between the dielectric material block and the metal film, (v) a photo detecting means for detecting the intensity of the light beam, which has been totally reflected from the interface described above, and (vi) analysis means for analyzing the state of surface plasmon resonance in accordance with the result of the detection having been made by the photo detecting means.

In order for the various different incidence angles described above to be obtained, a light beam having a comparatively small beam diameter may be caused to impinge upon the aforesaid interface with the incidence angle being altered. Alternatively, a light beam having a comparatively large beam diameter may be caused to impinge upon the aforesaid interface in a state of converged light or in a state of a divergent light, such that the light beam may contain components, which impinge at various different incidence angles upon the interface. In the former case, the reflected light beam, which is reflected from the interface with its reflection angle altering in accordance with the alteration of the incidence angle of the incident light beam, may be detected with a small photodetector, which moves by being interlocked with the alteration of the reflection angle, or may be detected with an area sensor extending in the direction of alteration of the reflection angle. In the latter case, the light beam may be detected with an area sensor extending in a direction such that the area sensor is capable of receiving all of the light beam components having been reflected from the interface at various different reflection angles.

With the surface plasmon sensor having the constitution described above, in cases where the light beam impinges at a specific incidence angle $\theta_{SP}$, which is not smaller than the total reflection angle, upon the metal film, an evanescent wave having an electric field distribution occurs in the sample, which is in contact with the metal film, and the surface plasmon is excited by the evanescent wave and at the interface between the metal film and the sample. In cases where the wave vector of the evanescent wave coincides with the wave vector of the surface plasmon, and wave number matching is thus obtained, the evanescent wave and the surface plasmon resonate, and energy of the light transfers to the surface plasmon. As a result, the intensity of the reflected light beam, which is totally reflected from the interface between the dielectric material block and the metal film, becomes markedly low. Ordinarily, the lowering of the intensity of the reflected light beam is detected as a dark line by the photo detecting means described above.

The resonance described above occurs only in cases where the incident light beam is P-polarized light. Therefore, it is necessary for the incident light beam to be set previously so as to impinge upon the aforesaid metal film as the P-polarized light.

The specific incidence angle $\theta_{SP}$, which is not smaller than the total reflection angle, and which is associated with the lowering of the intensity of the reflected light beam, will hereinbelow be referred to as the attenuated total reflection angle (ATR angle) $\theta_{SP}$. In cases where the wave number of the surface plasmon is found from the ATR angle $\theta_{SP}$, a dielectric constant of the sample is capable of being calculated. Specifically, the formula shown below obtains.

$$K_{SP}(\omega) = \frac{\omega}{c} \sqrt{\frac{\varepsilon_m(\omega)\varepsilon_s}{\varepsilon_m(\omega) + \varepsilon_s}}$$

wherein $K_{SP}$ represents the wave number of the surface plasmon, $\omega$ represents the angular frequency of the surface plasmon, $c$ represents the light velocity in a vacuum, $\in_m$ represents the dielectric constant of the metal, and $\in_s$ represents the dielectric constant of the sample.

Specifically, in cases where the dielectric constant $\in_s$ of the sample is found, the refractive index of the sample, or the like, is capable of being found in accordance with a predetermined calibration curve, or the like. Therefore, in cases where the ATR angle $\theta_{SP}$ is found, the dielectric constant $\in_s$ of the sample is capable of being calculated. Accordingly, the characteristics with regard to the refractive index of the sample are capable of being calculated.

As a similar sensor utilizing the evanescent wave, a leaky mode sensor has heretofore been known. (The leaky mode sensor is described in, for example, "Surface Refracto-sensor using Evanescent Waves: Principles and Instrumentations" Takayuki Okamoto, Bunko Kenkyu, Vol. 47, No. 1, 1998.) Basically, the leaky mode sensor comprises (i) a dielectric material block having, for example, a prism-like shape, (ii) a cladding layer, which is formed on one surface of the dielectric material block, (iii) an optical waveguide layer, which is formed on the cladding layer and is brought into contact with a sample, (iv) a light source for producing a light beam, (v) an optical system for irradiating the light beam to the dielectric material block at various different incidence angles such that a total reflection condition may be obtained at an interface between the dielectric material block and the cladding layer, (vi) photo detecting means for detecting the intensity of the light beam, which has been totally reflected from the interface described above, and (vii) analysis means for analyzing the state of excitation of a guided mode in accordance with the result of the detection having been made by the photo detecting means.

With the leaky mode sensor having the constitution described above, in cases where the light beam impinges at an incidence angle, which is not smaller than the total reflection angle, upon the cladding layer via the dielectric material block, only the light having a certain specific wave number, which light has impinged at a specific incidence angle upon the cladding layer, is propagated in the guided mode in the optical waveguide layer after passing through the cladding layer. In cases where the guided mode is thus excited, approximately all of the incident light is taken into the optical waveguide layer. Therefore, in such cases, the attenuated total reflection occurs, and the intensity of the light totally reflected from the aforesaid interface becomes markedly low. Also, the wave number of the guided optical wave depends upon the refractive index of the sample, which is located on the optical waveguide layer. Therefore, incases where the ATR angle $\theta_{SP}$ is detected, the refractive index of the sample and characteristics of the sample with regard to the refractive index of the sample are capable of being analyzed.

In the fields of pharmaceutical research, and the like, the surface plasmon sensor and the leaky mode sensor described above are often utilized for random screening for finding out a specific substance, which is capable of undergoing the binding with a desired sensing substance. In such cases, the sensing substance is fixed to the aforesaid thin film layer (the metal film in the cases of the surface plasmon sensor, or the combination of the cladding layer and the optical waveguide layer in the cases of the leaky mode sensor), and a liquid (a liquid sample) containing a test body is introduced on the sensing substance. Also, at each of stages after the passage of predetermined periods of time, the aforesaid ATR angle $\theta_{SP}$ is measured.

In cases where the test body contained in the liquid sample is a substance capable of undergoing the binding with the sensing substance, the refractive index of the sensing substance alters with the passage of time. Therefore, the aforesaid ATR angle $\theta_{SP}$ is measured at each of stages after the passage of predetermined periods of time, and a judgment is made as to whether an alteration of the ATR angle $\theta_{SP}$ has been or has not been occurred. In this manner, a judgment is capable of being made as to whether the binding of the test body with the sensing substance has or has not occurred, i.e. as to whether the test body is or is not the specific substance capable of undergoing the binding with the sensing substance. Examples of the combinations of the specific substances and the sensing substances include the combination of an antigen and an antibody and the combination of an antibody and a different antibody. Specifically, examples of the analyses with regard to the combinations of the specific substances and the sensing substances include an analysis, wherein a rabbit anti-human IgG antibody is employed as the sensing substance, a detection is made as to whether a human IgG antibody acting as the test body has or has not been bound to the rabbit anti-human IgG antibody, and a quantitative analysis of the human IgG antibody is made.

In order for the state of the binding of the test body, which is contained in the liquid sample, with the sensing substance to be detected, the ATR angle $\theta_{SP}$ itself need not necessarily be detected. Alternatively, for example, the liquid sample containing the test body may be introduced on the sensing substance, and thereafter the quantity of the alteration of the ATR angle $\theta_{SP}$ may be measured. Also, the state of the binding of the test body with the sensing substance may be detected in accordance with the quantity of the alteration of the ATR angle $\theta_{SP}$.

Also, the inventors proposed a sensor for detecting the state of the attenuated total reflection by use of an analysis chip, which has a well-like shape and is easy to process. (The proposed sensor is described in, for example, U.S. Pat. No. 6,597,456.) With the analysis chip having the well-like shape, in cases where, for example, a liquid sample is used as the sample, only a small amount of the liquid sample to be introduced into the analysis chip may be prepared for the analysis. Further, in cases where a table capable of supporting a plurality of analysis chips is utilized, analyses of various kinds of samples are capable of being made quickly and easily.

Furthermore, as the analysis apparatus of the type described above, there has been known a sensor for making an analysis, wherein a liquid sample is continuously supplied by use of a flow path means and onto a planar analysis chip, to which a sensing substance has been fixed. In cases where the sensor provided with the flow path means is utilized, during the detection of the state of the binding of the sensing substance and a specific substance with each other, the fresh liquid sample is continuously supplied onto the analysis chip. Therefore, the concentration of the test body contained in the liquid sample supplied onto the analysis chip does not alter, and the detection of the state of the binding is capable of being made accurately. Also, after it has been detected that the sensing substance and the specific substance have been bound to each other, a liquid sample containing no specific substance may be caused to flow on the analysis chip, to which the product of the binding of the sensing substance and the specific substance with each other has been fixed. In this manner, the state of separation of the sensing substance and the specific substance from each other is capable of being detected. Further, in cases where, for example, a gas is employed as the sample, or in cases where a liquid sample containing a gas is employed as the sample, the sample is capable of being easily supplied onto the analysis chip by use of the flow path means.

Also, recently, a wide variety of operations for detecting various kinds of reactions are performed, and various kinds of solvents for samples are utilized. Examples of the solvents include the solvents, such as water, which comparatively readily evaporate. The evaporation of water acting as the solvent results in an alteration of the refractive index of the sample and an alteration of the detection signal. In such cases, an accurate analysis is not capable of being made. In such cases, by the provision of the flow path means described above, the evaporation of the sample is capable of being suppressed, and a reliable detection signal is capable of being obtained.

As described above, by the provision of the flow path means, various effects are capable of being obtained. However, with the sensor provided with the flow path means, the problems occur in that, in order for the sample to be supplied continuously onto the analysis chip, it is necessary for a large amount of the sample to be prepared. Also, the problems occur in that the analyses of various kinds of samples are not capable of being made quickly.

As for the metal film, on which the surface plasmon resonance occurs, it is necessary for various kinds of proteins to be fixed to the metal film in accordance with the kinds of the reactions to be detected. However, ordinarily, the liquids containing the proteins are expensive. Therefore, it is desired that the liquids containing the proteins are capable of being utilized iteratively for the fixation of the proteins in the plurality of the wells.

In cases where the top surface of the metal film is widely open, a liquid containing a protein is capable of being supplied by use of an ordinarily utilized pipette, or the like, and then sucked up after a predetermined period of time necessary for the fixation has elapsed. (In certain cases, in order for the fixation to be promoted, the suction and the discharging of the liquid containing the protein may be iterated at the site.) The liquid containing the protein is thus capable of being recovered. Also, the recovered liquid containing the protein is then capable of being utilized for the fixation of the protein in a different well. In order for the protein fixation in the plurality of the well to be performed efficiently and easily, the top surface of the metal film should preferably be capable of being set to be widely open.

Further, as for certain kinds of analyses, it will be desired that the liquid sample is capable of being supplied onto the metal film by use of a flow path. Also, as for different kinds of analyses, it will be desired that, instead of the flow path being located, the liquid sample is capable of being supplied directly into the well. Therefore, it is desired that the analysis apparatus enables the selection of the supply of the liquid sample by use of the flow path or the supply of the liquid sample without the flow path being used.

Furthermore, there has been known a technique, wherein a reference signal is utilized such that errors in analysis results due to bulk effects, temperature changes, fluctuations of the light source, or the like, may be eliminated, and the analysis accuracy is thereby enhanced. In such cases, it is necessary that two kinds of analysis chips, i.e. an analysis chip for an analysis of a sample and an analysis chip for reference, be prepared.

Also, the analysis apparatuses, such as the surface plasmon sensors or the leaky mode sensors, are required to have a fine angle accuracy. Therefore, besides the reference analysis, it is desired that two kinds of analyses be capable of being made simultaneously in one analysis chip, in which the measurement conditions are kept approximately identical, at the time of experiments for comparison, and the like.

SUMMARY OF THE INVENTION

The primary object of the present invention is to provide an analysis method, wherein a flow path for supplying a sample is capable of being used selectively, wherein two kinds of analyses are capable of being made simultaneously in one analysis chip, and wherein an ordinary analysis, which is made with the sample being retained in the analysis chip, and an analysis, which is made with the sample being supplied continuously into the analysis chip, are capable of being performed.

Another object of the present invention is to provide an analysis apparatus for carrying out the analysis method.

The specific object of the present invention is to provide an analysis unit for use in the analysis method and apparatus.

The present invention provides an analysis method, comprising the steps of:

i) preparing a well-shaped analysis chip, which is provided with a dielectric material block transparent with respect to a light beam having been produced by a light source, a thin film layer formed on one surface of the dielectric material block, and a sample support section capable of supporting a sample on a surface of the thin film layer, the thin film layer being provided with two different regions, which have different characteristics, on the surface of the thin film layer, ii) releasably loading a flow path unit into the well-shaped analysis chip, the flow path unit being provided with a supply path, through which the sample is supplied onto the surface of the thin film layer, and a discharging path, through which the sample is discharged from the surface of the thin film layer, iii) irradiating the light beam, which has been produced by the light source, to each of a first interface, which is an interface between one of the two different regions of the thin film layer and the dielectric material block, and a second interface, which is an interface between the other region of the thin film layer and the dielectric material block, in a parallel manner and at an incidence angle such that a total reflection condition is obtained at each of the first interface and the second interface, iv) detecting each of an intensity of the light beam, which has been totally reflected from the first interface, and an intensity of the light beam, which has been totally reflected from the second interface, with independent detecting operations, and v) acquiring refractive index information with regard to a substance to be analyzed, which is located on the thin film layer, in accordance with results of the detection of the light beam intensities.

The present invention also provides an analysis apparatus, comprising:

i) a light source for producing a light beam, ii) a well-shaped analysis chip, which is provided with a dielectric material block transparent with respect to the light beam having been produced by the light source, a thin film layer formed on one surface of the dielectric material block, and a sample support section capable of supporting a sample on a surface of the thin film layer, the thin film layer being provided with two different regions, which have different characteristics, on the surface of the thin film layer, iii) a flow path unit, which is releasably loaded into the well-shaped analysis chip, the flow path unit being provided with a supply path, through which the sample is supplied onto the surface of the thin film layer, and a discharging path, through which the sample is discharged from the surface of the thin film layer, iv) an optical system for irradiating the light beam, which has been produced by the light source, to each of a first interface, which is an interface between one of the two different regions of the thin film layer and the dielectric material block, and a second interface, which is an interface between the other region of the thin film layer and the dielectric material block, in a parallel manner and at an incidence angle such that a total reflection condition is obtained at each of the first interface and the second interface, v) photo detecting means for detecting each of an intensity of the light beam, which has been totally reflected from the first interface, and an intensity of the light beam, which has been totally reflected from the second interface, with independent detecting operations, and vi) refractive index information acquiring means for acquiring refractive index information with regard to a substance to be analyzed, which is located on the thin film layer, in accordance with results of the detection of the light beam intensities, which detection has been made by the photo detecting means.

Each of the analysis method and the analysis apparatus in accordance with the present invention should preferably be modified such that either one of the two different regions of the thin film layer is a reference signal measuring region, which is free from characteristics of undergoing reaction with the sample.

Also, each of the analysis method and the analysis apparatus in accordance with the present invention may be modified such that the two different regions of the thin film layer have axisymmetric shapes formed with a straight line, which connects a center point of an outlet of the supply path and a center point of an inlet of the discharging path with each other, being taken as an axis of symmetry.

Alternatively, each of the analysis method and the analysis apparatus in accordance with the present invention may be modified such that the two different regions of the thin film layer have axisymmetric shapes formed with a perpendicular bisector of a straight line, which connects a center point of an outlet of the supply path and a center point of an inlet of the discharging path with each other, being taken as an axis of symmetry.

Further, the analysis method in accordance with the present invention may be modified such that the detection of each of the intensity of the light beam, which has been totally reflected from the first interface, and the intensity of the light beam, which has been totally reflected from the second interface, is performed while the supply of the sample to the flow path unit is being ceased.

Furthermore, the analysis apparatus in accordance with the present invention may be modified such that the photo detecting means performs the detection of each of the intensity of the light beam, which has been totally reflected from the first interface, and the intensity of the light beam, which has been totally reflected from the second interface, while the supply of the sample to the flow path unit is being ceased.

The present invention further provides an analysis unit, comprising:

i) a well-shaped analysis chip, which is provided with a dielectric material block transparent with respect to a light beam, a thin film layer formed on one surface of the dielectric material block, and a sample support section capable of supporting a sample on a surface of the thin film layer, the thin film layer being provided with two different regions, which have different characteristics, on the surface of the thin film layer, and ii) a flow path unit, which is releasably loaded into the well-shaped analysis chip, the flow path unit being provided with a supply path, through which the sample is supplied onto the surface of the thin film layer, and a discharging path, through which the sample is discharged from the surface of the thin film layer.

The analysis unit in accordance with the present invention should preferably be modified such that either one of the two different regions of the thin film layer is a reference signal measuring region, which is free from characteristics of undergoing reaction with the sample.

Also, the analysis unit in accordance with the present invention may be modified such that the two different regions of the thin film layer have axisymmetric shapes formed with a straight line, which connects a center point of an outlet of the supply path and a center point of an inlet of the discharging path with each other, being taken as an axis of symmetry.

Alternatively, the analysis unit in accordance with the present invention may be modified such that the two different regions of the thin film layer have axisymmetric shapes formed with a perpendicular bisector of a straight line, which connects a center point of an outlet of the supply path and a center point of an inlet of the discharging path with each other, being taken as an axis of symmetry.

The analysis method in accordance with the present invention may be constituted as a surface plasmon analysis method, wherein a metal film is utilized as the thin film layer, and wherein an analysis is made by the utilization of the effects of the surface plasmon resonance. Also, the analysis method in accordance with the present invention may be constituted as a leaky mode analysis method, wherein a combination of a cladding layer, which is formed on one surface of the dielectric material block, and an optical waveguide layer, which is formed on the cladding layer, is utilized as the thin film layer, and wherein an analysis is made by the utilization of the effects of the excitation of the guided mode in the optical waveguide layer.

Further, each of the analysis apparatus and the analysis unit in accordance with the present invention may be constituted as a surface plasmon sensor, wherein a metal film is utilized as the thin film layer, and wherein an analysis is made by the utilization of the effects of the surface plasmon resonance. Furthermore, each of the analysis apparatus and the analysis unit in accordance with the present invention may be constituted as a leaky mode sensor, wherein a combination of a cladding layer, which is formed on one surface of the dielectric material block, and an optical waveguide layer, which is formed on the cladding layer, is utilized as the thin film layer, and wherein an analysis is made by the utilization of the effects of the excitation of the guided mode in the optical waveguide layer.

In each of the analysis method and the analysis apparatus in accordance with the present invention, the refractive index information with regard to the substance to be analyzed, which is located on the thin film layer, is acquired. Specifically, for example, the information representing the refractive index itself of the sample, which is located on the thin film layer, may be acquired. Alternatively, a sensing substance, such as an antibody, may be fixed on the thin film layer, and the information representing an alteration of the refractive index occurring due to an antigen-antibody reaction may be acquired. As another alternative, a sensing substance, such as an antibody, may be fixed on the thin film layer, and the information representing the presence or absence of an alteration of the refractive index occurring due to an antigen-antibody reaction may be acquired.

The acquisition of the refractive index information may be performed with a technique, wherein a light beam is irradiated to the interface between a dielectric material block and a thin film layer at various different incidence angles, the light beam having been reflected from the interface is detected, the ATR angle $\theta_{SP}$ or an alteration of the ATR angle $\theta_{SP}$ is detected, and the information representing the refractive index or the information representing an alteration of the refractive index is thereby acquired.

Alternatively, the acquisition of the refractive index information may be performed with a technique, wherein a light beam containing light components having a plurality of different wavelengths is irradiated to the interface between a dielectric material block and a thin film layer at an incidence angle such that the total reflection condition may be obtained at the interface, the intensity of each of the light components having the different wavelengths, which light components have been totally reflected from the interface, is detected, the degree of the attenuated total reflection is detected with respect to each of the light components having the different wavelengths, and the information representing the refractive index or the information representing an alteration of the refractive index is thereby acquired. (The technique utilizing the light beam containing the light components having the plurality of the different wavelengths is described in, for example, "Porous Gold in Surface Plasmon Resonance Measurement" D. V. Noort, K. Johansen, and C.-F. Mandenius, EUROSENSORS XIII, pp. 585-588, 1999.)

As another alternative, the acquisition of the refractive index information may be performed with a technique, wherein a light beam is irradiated to the interface between a dielectric material block and a thin film layer at an incidence angle such that the total reflection condition may be obtained at the interface, part of the light beam before impinging upon the interface is split from the light beam, the split part of the light beam is subjected to interference with the light beam, which has been totally reflected from the interface, an alteration of interference fringes of the light beam having been subjected to the interference is detected, and the information representing an alteration of the refractive index is thereby acquired. (The technique utilizing the interference of the light beam is described in, for example, "Surface Plasmon Resonance Interferometry for Micro-Array Biosensing" P. I. Nikitin, A. N. Grigorenko, A. A. Beloglazov, M. V. Valeiko, A. I. Savchuk, and O. A. Savchuk, EUROSENSORS XIII, pp. 235-238, 1999.)

Specifically, the refractive index information with regard to the substance to be analyzed may be one of various kinds of information altering in accordance with the refractive index of the substance to be analyzed. Examples of the various kinds of information altering in accordance with the refractive index of the substance to be analyzed include the information representing the ATR angle $\theta_{SP}$, which alters in accordance with the refractive index of the substance to be analyzed, the information representing a light beam wavelength associated with the occurrence of the attenuated total reflection, which light beam wavelength alters in accordance with the refractive index of the substance to be analyzed, the information representing an alteration of the ATR angle $\theta_{SP}$, which alteration occurs in accordance with an alteration of the refractive index of the substance to be analyzed, the information representing an alteration of a light beam wavelength associated with the occurrence of the attenuated total reflection, which alteration occurs in accordance with an alteration of the refractive index of the substance to be analyzed, and the information representing an alteration of interference fringes, which alteration occurs in accordance with an alteration of the refractive index of the substance to be analyzed.

With each of the analysis method and the analysis apparatus in accordance with the present invention, the thin film layer is provided with the two different regions, which have different characteristics. Also, the light beam, which has been produced by the light source, is irradiated to each of the first interface, which is the interface between one of the two different regions of the thin film layer and the dielectric material block, and the second interface, which is the interface between the other region of the thin film layer and the dielectric material block, in the parallel manner and at the incidence angle such that the total reflection condition is obtained at each of the first interface and the second interface. The refractive index information with regard to the substance to be analyzed, which is located on the thin film layer, is thus acquired. Therefore, with each of the analysis method and the analysis apparatus in accordance with the present invention, two kinds of analyses are capable of being made simultaneously by use of one analysis chip.

Also, with each of the analysis method and the analysis apparatus in accordance with the present invention, the flow path unit is releasably loaded into the well-shaped analysis chip. The flow path unit is provided with the supply path, through which the sample is supplied onto the surface of the thin film layer, and the discharging path, through which the sample is discharged from the surface of the thin film layer. Therefore, with each of the analysis method and the analysis apparatus in accordance with the present invention, the ordinary analysis, which is made with the sample being retained within the analysis chip, and the analysis, which is made with the sample being supplied continuously into the analysis chip, are capable of being performed.

With each of the analysis method and the analysis apparatus in accordance with the present invention, wherein either one of the two different regions of the thin film layer is the reference signal measuring region, which is free from characteristics of undergoing reaction with the sample, a sample analysis and a reference measurement are capable of being performed by use of one analysis chip.

With the analysis unit in accordance with the present invention, wherein the thin film layer is provided with the two different regions, which have different characteristics, two kinds of analyses are capable of being made simultaneously by use of one analysis chip.

Also, the analysis unit in accordance with the present invention comprises the flow path unit, which is releasably loaded into the well-shaped analysis chip. The flow path unit is provided with the supply path, through which the sample is supplied onto the surface of the thin film layer, and the discharging path, through which the sample is discharged from the surface of the thin film layer. Therefore, with the analysis unit in accordance with the present invention, the ordinary analysis, which is made with the sample being retained within the analysis chip, and the analysis, which is made with the sample being supplied continuously into the analysis chip, are capable of being performed.

With the analysis unit in accordance with the present invention, wherein either one of the two different regions of the thin film layer is the reference signal measuring region, which is free from characteristics of undergoing reaction with the sample, a sample analysis and a reference measurement are capable of being performed by use of one analysis chip.

BRIEF DESCRIPTION OF THE DRAWINGS

FIG. 8 is a side view showing a measuring system in a second embodiment of the analysis apparatus in accordance with the present invention, which second embodiment is constituted as a leaky mode sensor.

DESCRIPTION OF THE PREFERRED EMBODIMENTS

The present invention will hereinbelow be described in further detail with reference to the accompanying drawings.

Figure 1:
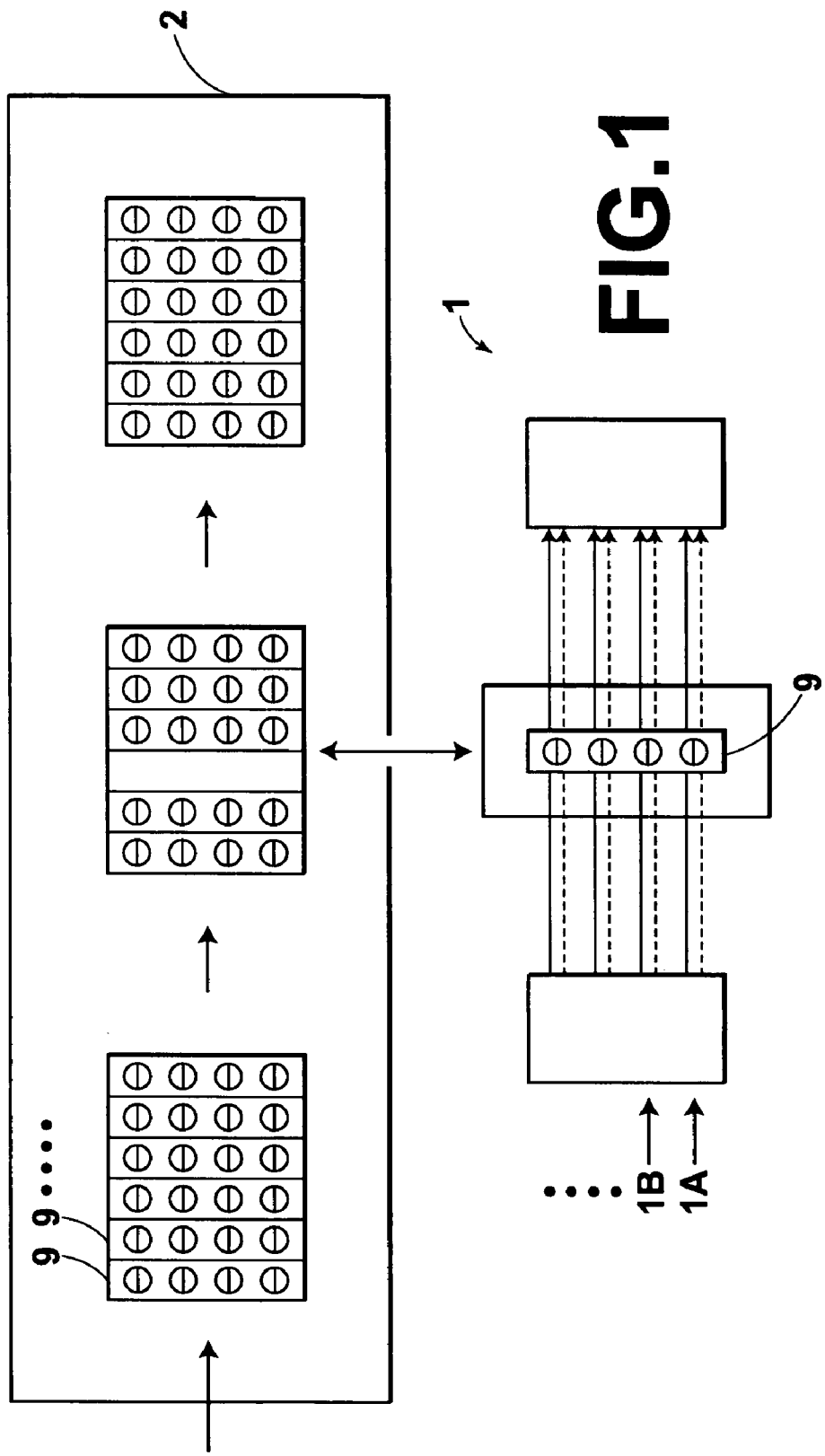
FIG. 1 is a schematic plan view showing a first embodiment of the analysis apparatus in accordance with the present invention, which is constituted as a surface plasmon sensor.
Figure 2:
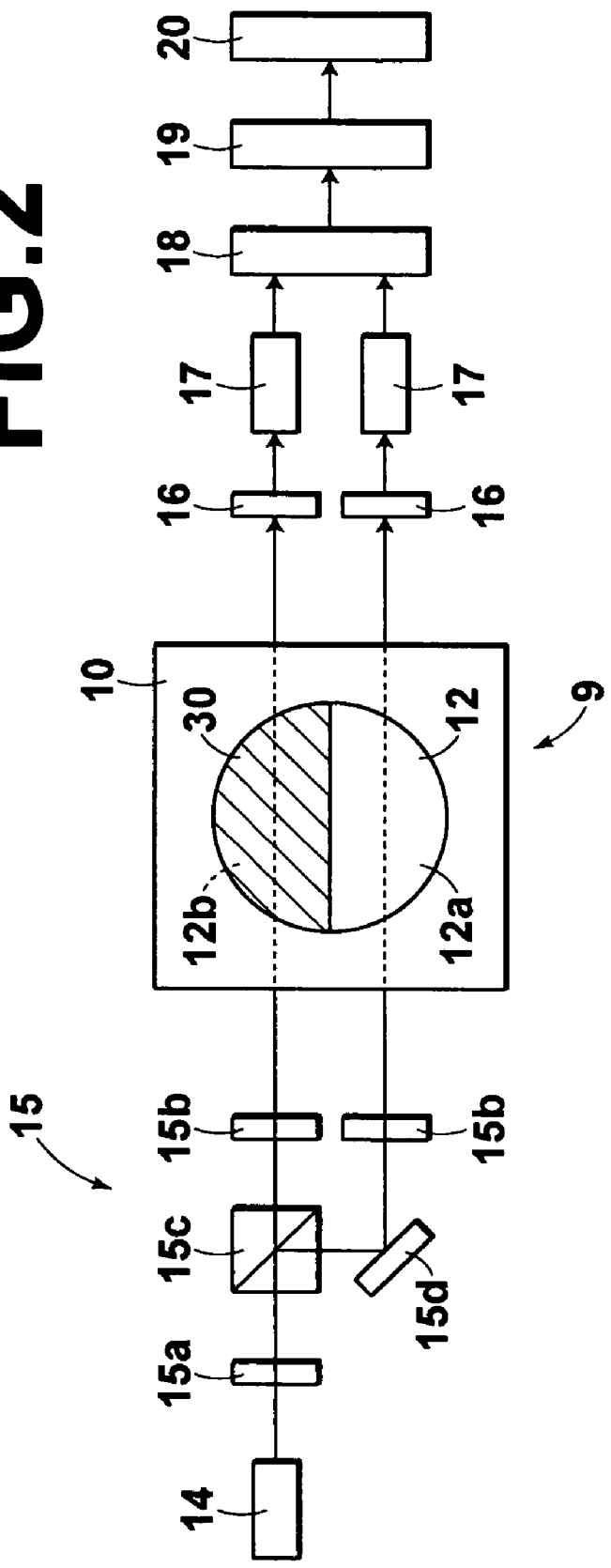
FIG. 2 is a plan view showing a measuring system of the surface plasmon sensor of FIG. 1.
Figure 3:
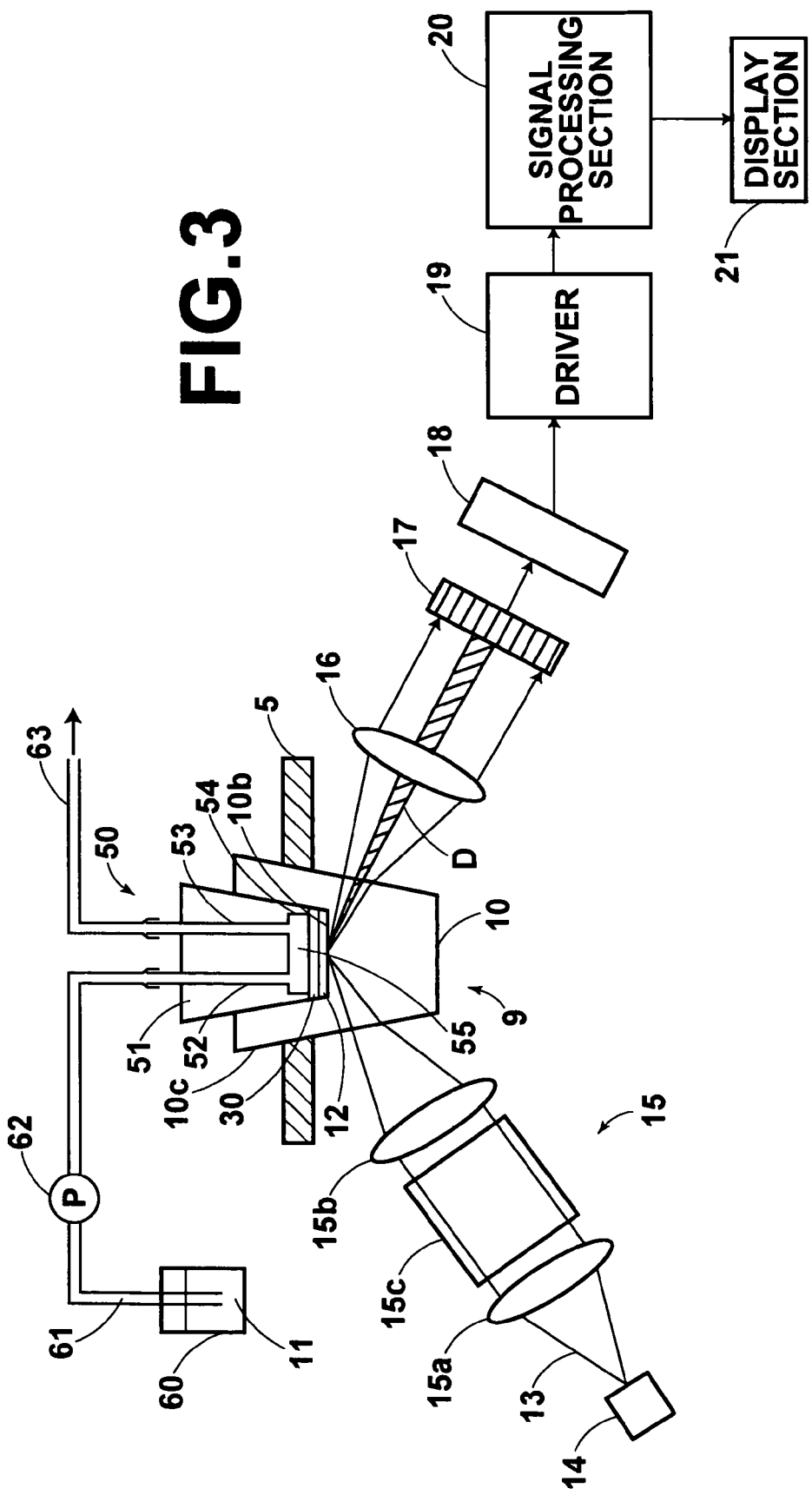
FIG. 3 is a side view showing the measuring system of the surface plasmon sensor of FIG. 1.

A first embodiment of the analysis apparatus in accordance with the present invention is constituted as a surface plasmon sensor, wherein light beams are irradiated to a plurality of wells in a parallel manner, and wherein analyses of a plurality of samples are thus capable of being made simultaneously. FIG. 1 is a schematic plan view showing the first embodiment of the analysis apparatus in accordance with the present invention, which is constituted as the surface plasmon sensor. FIG. 2 is a plan view showing a measuring system of the surface plasmon sensor of FIG. 1. FIG. 3 is a side view showing the measuring system of the surface plasmon sensor of FIG. 1.

With reference to FIG. 1, a surface plasmon sensor 1, which is the first embodiment of the analysis apparatus in accordance with the present invention, comprises a plurality of surface plasmon measuring systems 1A, 1B, . . . , which have identical constitutions. The constitution of each of the measuring systems 1A, 1B, . . . will be described hereinbelow. In the explanation made below, the suffixes A, B, . . . for representing the respective elements of the measuring systems 1A, 1B, . . . will be omitted for facilitating the explanation. As illustrated in FIG. 2 and FIG. 3, each of the measuring systems 1A, 1B, . . . comprises a well-shaped analysis chip 9. The analysis chip 9 is provided with a dielectric material block 10. By way of example, the dielectric material block 10 has an approximately truncated quadrangular pyramid-like shape. The analysis chip 9 is also provided with a metal film 12, which is formed on one surface of the dielectric material block 10 (i.e., the top surface of the dielectric material block 10 in FIG. 3). The metal film 12 is made from gold, silver, copper, aluminum, or the like.

The dielectric material block 10 is made from, for example, a transparent resin. As illustrated in FIG. 3, the dielectric material block 10 has a shape such that the areas around the area, on which the metal film 12 is formed, are raised. The raised areas of the dielectric material block 10 act as a sample support section 10c for supporting a liquid sample 11. Also, as illustrated in FIG. 2, the metal film 12 is divided into two regions 12a and 12b having different characteristics. A sensing substance 30 is fixed to the region 12b. The sensing substance 30 will be described later.

As illustrated in FIG. 3, a flow path unit 50 for forming a flow path on the combination of the metal film 12 and the sensing substance 30 is releasably loaded into the sample support section 10c of the analysis chip 9. The flow path unit 50 comprises a flow path holder 51, which is fitted into the sample support section 10c of the dielectric material block 10. The flow path unit 50 also comprises a supply path 52, through which a liquid sample is supplied, and a discharging path 53, through which the liquid sample is discharged. The supply path 52 and the discharging path 53 extend through the flow path holder 51. The flow path unit 50 is capable of being easily loaded into and released from the analysis chip 9.

An outlet of the supply path 52 and an inlet of the discharging path 53 are open at the bottom of the flow path holder 51. Also, a sealing section 54, which surrounds the outlet of the supply path 52 and the inlet of the discharging path 53, is located at the area of the bottom of the flow path holder 51, which area comes into contact with the surface of the combination of the metal film 12 and the sensing substance 30. Therefore, as illustrated in FIG. 3, in cases where the flow path unit 50 is fitted into the analysis chip 9, a measurement flow path 55 is formed at the inside of the space defined by the sealing section 54. The sealing section 54 may be combined with the top part of the flow path holder 51 into an integral body. Alternatively, the sealing section 54 may be made from a material different from the material of the top part of the flow path holder 51 and may be fitted to the top part of the flow path holder 51. By way of example, an O-ring acting as the sealing section 54 may be fitted to the bottom part of the flow path holder 51.

Figure 4:
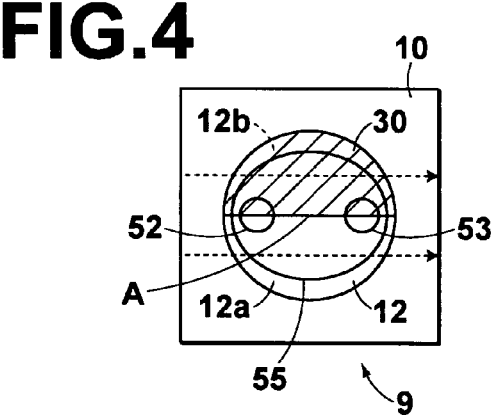
FIG. 4 is a plan view showing an example of a liquid sample flow path within an analysis chip.

As illustrated in FIG. 4, the two regions 12a and 12b of the metal film 12 have axisymmetric shapes formed with a straight line A, which connects a center point of an outlet of the supply path 52 and a center point of an inlet of the discharging path 53 with each other, being taken as an axis of symmetry. Also, the measurement flow path 55 defined by the sealing section 54 is constituted of two regions having axisymmetric shapes formed with the straight line A, which connects the center point of the outlet of the supply path 52 and the center point of the inlet of the discharging path 53 with each other, being taken as the axis of symmetry. Therefore, the condition of the supply of the liquid sample 11 to the region 12a and the condition of the supply of the liquid sample 11 to the region 12b are capable of being set to be identical. If the width of the measurement flow path 55 defined by the sealing section 54, which width is taken in the direction normal to the straight line A, is markedly large, uniformity of the liquid sample 11 within the measurement flow path 55 will become bad. Accordingly, the width of the measurement flow path 55 defined by the sealing section 54, which width is taken in the direction normal to the straight line A, should preferably be as small as possible.

Reverting to FIG. 3, the supply path 52 of the flow path unit 50 is connected by a pipe 61 to a pump 62. The pump 62 is connected to a liquid reservoir 60. The liquid sample 11 containing a test body is accommodated previously in the liquid reservoir 60. Also, the discharging path 53 is connected to a pipe 63, through which the liquid sample 11 having been discharged from the flow path unit 50 flows out into a drainage section (not shown).

As illustrated in FIG. 2 and FIG. 3, besides the dielectric material block 10 described above, each of the measuring systems 1A, 1B, . . . also comprises a laser beam source 14 for producing one laser beam 13. The laser beam source 14 may be constituted of, for example, a semiconductor laser. Each of the measuring systems 1A, 1B, . . . further comprises an optical system 15 for irradiating the laser beam 13, which has been produced by the laser beam source 14, to the dielectric material block 10, such that the laser beam 13 impinges upon each of an interface 10a, which is the interface between the dielectric material block 10 and the region 12a of the metal film 12, and an interface 10b, which is the interface between the dielectric material block 10 and the region 12b of the metal film 12, at various different incidence angles and in a parallel manner. Each of the measuring systems 1A, 1B, ... still further comprises two collimator lenses 16, 16. Each of the collimator lenses 16, 16 collimates one of the laser beam 13, which has been totally reflected from the interface 10a, and the laser beam 13, which has been totally reflected from the interface 10b. Each of the measuring systems 1A, 1B, ... also comprises two photodiode arrays 17, 17. Each of the photodiode arrays 17, 17 detects one of the laser beam 13, which has been totally reflected from the interface 10a and has then been collimated by the corresponding collimator lens 16, and the laser beam 13, which has been totally reflected from the interface 10b and has then been collimated by the corresponding collimator lens 16. Each of the measuring systems 1A, 1B, . . . further comprises a differential amplifier array 18, which is connected to the two photodiode arrays 17, 17. Each of the measuring systems 1A, 1B, . . . still further comprises a driver 19. Each of the measuring systems 1A, 1B, ... also comprises a signal processing section 20, which is constituted of a computer system, or the like. Each of the measuring systems 1A, 1B, ... further comprises a display section 21, which is connected to the signal processing section 20.

The optical system 15 comprises a collimator lens 15a for collimating the laser beam 13, which has been radiated out in a state of divergent light from the laser beam source 14. The optical system 15 also comprises a semi-transparent mirror 15c for splitting the collimated laser beam 13 into two beams. The optical system 15 further comprises a mirror 15d for reflecting the laser beam 13, which has been reflected by the semi-transparent mirror 15c, toward the analysis chip 9. The optical system 15 still further comprises two converging lenses 15b, 15b. One of the converging lenses 15b, 15b converges the laser beam 13, which has passed through the semi-transparent mirror 15c, onto the interface 10b described above. The other converging lens 15b converges the laser beam 13, which has been reflected by the mirror 15d, onto the interface 10a described above. The laser beam 13 is converged onto each of an area of the interface 10a and an area of the interface 10b, which areas are located within the measurement flow path 55.

The laser beam 13 is converged in the manner described above. Therefore, the laser beam 13 contains laser beam components, which impinge at various different incidence angles θ upon each of the interface 10a and the interface 10b. The incidence angles θ upon each of the interface 10a and the interface 10b are set to be not smaller than the total reflection angle. Therefore, the laser beam 13 is totally reflected from each of the interface 10a and the interface 10b. Also, the laser beam 13, which has been reflected from each of the interface 10a and the interface 10b, contains the laser beam components, which have been reflected at various different reflection angles. The optical system 15 may be constituted such that the laser beam 13 impinges in a defocused state upon each of the interface 10a and the interface 10b. In such cases, errors in detection of the state of the surface plasmon resonance are capable of being averaged, and the analysis accuracy is capable of being enhanced.

The laser beam 13 is irradiated so as to impinge as P-polarized light upon each of the interface 10a and the interface 10b. In order for the laser beam 13 to impinge as the P-polarized light upon each of the interface 10a and the interface 10b, the laser beam source 14 may be located such that the direction of polarization of the laser beam 13 may coincide with the predetermined direction described above. Alternatively, the direction of polarization of the laser beam 13 may be controlled by use of a wave plate.

How an analysis of a sample is made with the surface plasmon sensor 1 having the constitution described above will be described hereinbelow.

Before the measurement is made, the analysis chip 9 is processed from a constant temperature chamber 2 and secured at an analysis chip support section 5 of the measuring system. Thereafter, the flow path unit 50 is loaded into the analysis chip 9, such that the sealing section 54 of the flow path unit 50 comes into close contact with the combination of the metal film 12 and the sensing substance 30. Also, the pump 62 is actuated, and the liquid sample 11, which is accommodated in the liquid reservoir 60, is continuously supplied to the measurement flow path 55 through the supply path 52 of the flow path unit 50. The liquid sample 11, which has passed through the measurement flow path 55, discharged into the drainage section through the discharging path 53.

After the liquid sample 11 has been supplied into the measurement flow path 55, the measurement is begun. As described above, while the measurement is being made, the liquid sample 11 is supplied continuously to the measurement flow path 55. As illustrated in FIG. 3, the laser beam 13, which has been radiated out in the state of divergent light from the laser beam source 14, is converged by the effects of the optical system 15 onto each of the interface 10a and the interface 10b between the dielectric material block 10 and the metal film 12, which interfaces are located below the measurement flow path 55. At this time, the laser beam 13 contains the laser beam components, which impinge at various different incidence angles θ upon each of the interface 10a and the interface 10b. The incidence angles θ upon each of the interface 10a and the interface 10b are set to be not smaller than the total reflection angle. Therefore, the laser beam 13 is totally reflected from each of the interface 10a and the interface 10b. Also, the laser beam 13, which has been reflected from each of the interface 10a and the interface 10b, contains the laser beam components, which have been reflected at various different reflection angles.

The laser beam 13, which has been totally reflected from the interface 10a and has then been collimated by one of the two collimator lenses 16, 16, and the laser beam 13, which has been totally reflected from the interface 10b and has then been collimated by the other collimator lens 16, are detected respectively by the two photodiode arrays 17, 17. In this embodiment, each of the two photodiode arrays 17, 17 comprises a plurality of photodiodes 17a, 17b, 17c, . . . , which arrayed in a line. Each of the two photodiode arrays 17, 17 is located in an orientation such that the array direction of the photodiodes 17a, 17b, 17c, ... is approximately normal to the direction of travel of the collimated laser beam 13 in the plane of the sheet of FIG. 3. Therefore, each of the laser beam components of the laser beam 13, which laser beam components have been totally reflected at various different reflection angles from one of the interface 10a and the interface 10b, is received by one of the different photodiodes 17a, 17b, 17c, ...

Figure 5:
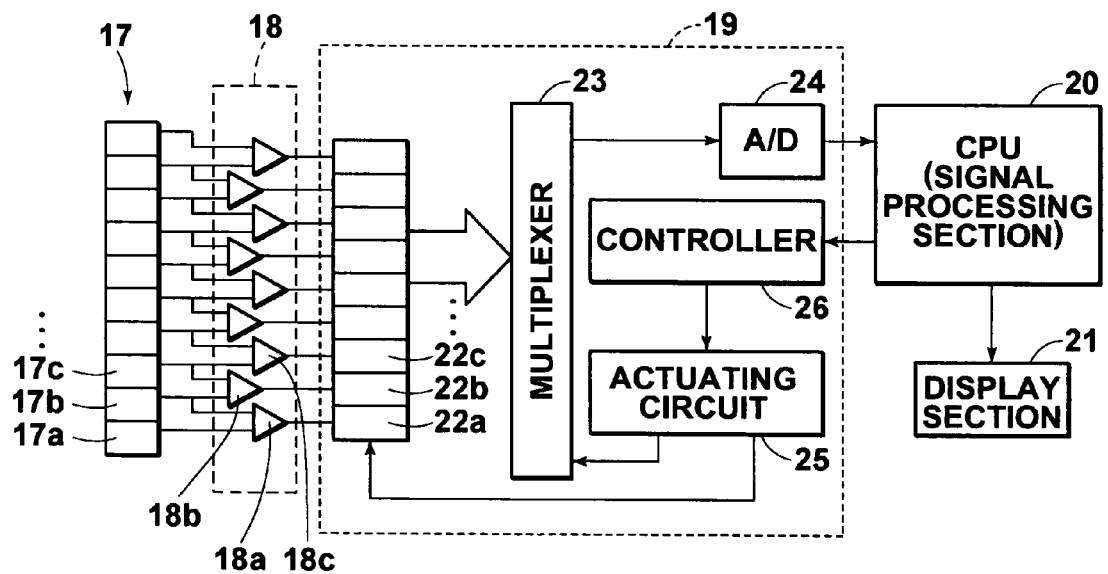
FIG. 5 is a block diagram showing an electrical constitution of the measuring system of the surface plasmon sensor of FIG. 1.

FIG. 5 is a block diagram showing an electrical constitution of the measuring system of the surface plasmon sensor 1 of FIG. 1. As illustrated in FIG. 5, the driver 19 described above comprises sample and hold circuits 22a, 22b, 22c, . . . , each of which samples and holds the output of one of differential amplifiers 18a, 18b, 18c, ... of the differential amplifier array 18. The driver 19 also comprises a multiplexer 23 for receiving the outputs of the sample and hold circuits 22a, 22b, 22c, ... The driver 19 further comprises an analog-to-digital converter 24 for digitizing the output of the multiplexer 23 and feeding the digital output into the signal processing section 20. The driver 19 still further comprises an actuating circuit 25 for actuating the multiplexer 23 and the sample and hold circuits 22a, 22b, 22c, . . . The driver 19 also comprises a controller 26 for controlling the operations of the actuating circuit 25 in accordance with an instruction given by the signal processing section 20. The differential amplifier array 18, the driver 19, and the signal processing section 20 are constituted so as to perform identical processing in a parallel manner on the inputs fed from the two photodiode arrays 17, 17.

The outputs of the photodiodes 17a, 17b, 17c, . . . are fed into the differential amplifiers 18a, 18b, 18c, . . . of the differential amplifier array 18. At this time, the outputs of two adjacent photodiodes are fed into one common differential amplifier. Therefore, it may be regarded that the output of each of the differential amplifiers 18a, 18b, 18c, . . . represents one of differentiation values obtained from differentiation processing, which is performed on the photo detection signal components obtained from the plurality of the photodiodes 17a, 17b, 17c, . . . and is performed with respect to the array direction of the photodiodes 17a, 17b, 17c, . . . .

The output of each of the differential amplifiers 18a, 18b, 18c, . . . is sampled and held with predetermined timing by the corresponding one of the sample and hold circuits 22a, 22b, 22c, . . . and is fed into the multiplexer 23. The multiplexer 23 feeds the outputs of the differential amplifiers 18a, 18b, 18c, . . . , which outputs have been sampled and held by the sample and hold circuits 22a, 22b, 22c, . . . , in predetermined order into the analog-to-digital converter 24. The analog-to-digital converter 24 digitizes the received outputs and feeds the digital outputs into the signal processing section 20.

Figure 6A:
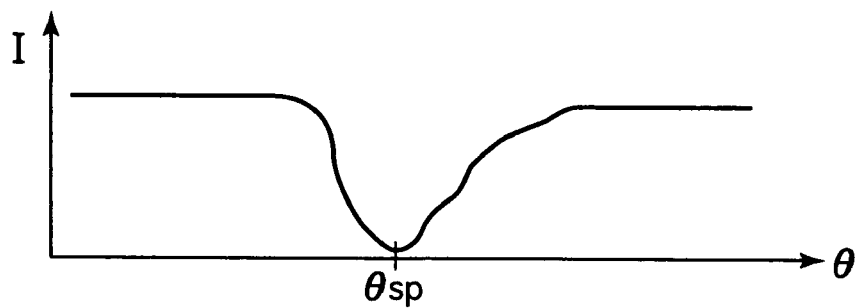
FIG. 6A is a graph showing relationship between an incidence angle of a light beam upon an interface and a detected optical intensity of the light beam, which has been totally reflected from the interface, in the measuring system of the surface plasmon sensor of FIG. 1.

FIG. 6A is a graph showing the relationship between the incidence angle $\theta$ of the laser beam 13 upon the interface 10a (or the interface 10b) and a detected optical intensity I of the laser beam 13, which has been totally reflected from the interface 10a (or the interface 10b), in the measuring system of the surface plasmon sensor 1 of FIG. 1.

The laser beam 13, which has impinged at the specific incidence angle $\theta_{SP}$ upon the interface 10a (or the interface 10b), excites the surface plasmon at the interface between the metal film 12 and the liquid sample 11. Therefore, as for the laser beam 13, which has impinged at the specific incidence angle $\theta_{SP}$ upon the interface 10a (or the interface 10b), the optical intensity I of the laser beam 13, which has been totally reflected from the interface 10a (or the interface 10b), becomes markedly low. Specifically, the specific incidence angle $\theta_{SP}$ represents the ATR angle $\theta_{SP}$. At the ATR angle $\theta_{SP}$, the optical intensity I of the reflected laser beam 13 takes the minimum value. As indicated by D in FIG. 3, the lowering of the optical intensity I of the reflected laser beam 13 appears as a dark line in the reflected laser beam 13.

Figure 6B:
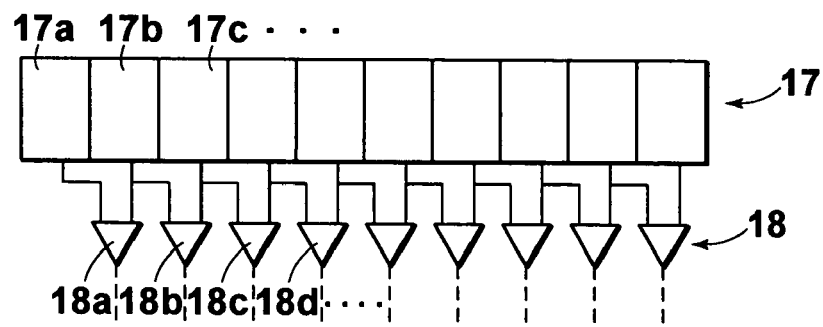
FIG. 6B is an explanatory view showing photodiodes arrayed in a direction in the measuring system of the surface plasmon sensor of FIG. 1.

FIG. 6B is an explanatory view showing the photodiodes 17a, 17b, 17c, . . . arrayed in a direction in the measuring system of the surface plasmon sensor 1 of FIG. 1. As described above, the position of each of the photodiodes 17a, 17b, 17c, . . . , which position is taken with respect to the array direction of the photodiodes 17a, 17b, 17c, uniquely corresponds to the incidence angle $\theta$.

Figure 6C:
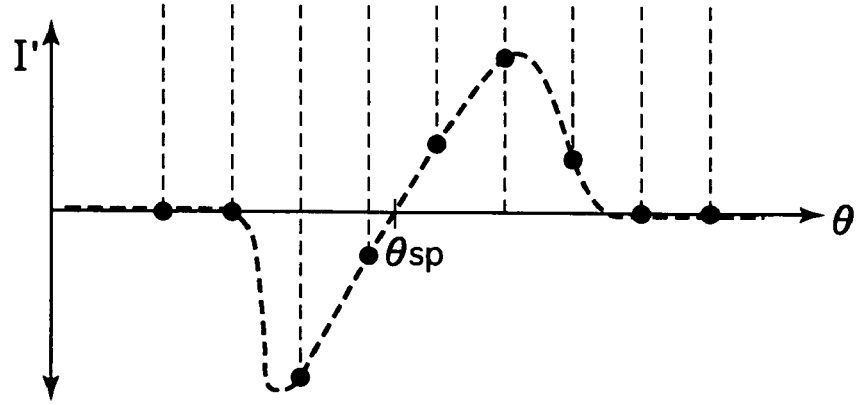
FIG. 6C is a graph showing relationship between the incidence angle of the light beam upon the interface and a differentiation value of values of an optical intensity detection signal representing the optical intensity of the light beam, which has been totally reflected from the interface, in the measuring system of the surface plasmon sensor of FIG. 1.

FIG. 6C is a graph showing the relationship between the position of each of the photodiodes 17a, 17b, 17c, . . . , which position is taken with respect to the array direction of the photodiodes 17a, 17b, 17c, . . . , i.e. the incidence angle $\theta$, and an output I' of each of the differential amplifiers 18a, 18b, 18c, . . . (i.e., the differentiation value of the values of the optical intensity I of the reflected laser beam 13).

In accordance with the outputs I', which are received from the analog-to-digital converter 24 and represents the differentiation values, the signal processing section 20 selects a differential amplifier (in the case of FIGS. 6A, 6B, and 6C, the differential amplifier 18d), which yields the output closest to the differentiation value I'=0 corresponding to the ATR angle $\theta_{SP}$, from among the differential amplifiers 18a, 18b, 18c, . . . Also, the signal processing section 20 performs predetermined correction processing on the differentiation value I', which is outputted from the thus selected differential amplifier. The signal processing section 20 feeds the information, which represents the differentiation value I' having been subjected to the predetermined correction processing, into the display section 21. It may often occur that a certain differential amplifier yields the output representing the differentiation value I'=0 corresponding to the ATR angle $\theta_{SP}$. In such cases, the certain differential amplifier described above is selected.

Thereafter, at each of the stages after the passage of the predetermined periods of time, the differentiation value I', which has been outputted from the selected differential amplifier 18d and has then been subjected to the predetermined correction processing, is displayed on the display section 21. In cases where the dielectric constant of the substance, which is in contact with the metal film 12 of the analysis chip 9, i.e. the refractive index of the substance, alters, and the ATR angle $\theta_{SP}$ alters such that the curve illustrated in FIG. 6A shifts horizontally in FIG. 6A, the differentiation value I' alters vertically in FIG. 6C in accordance with the alteration of the ATR angle $\theta_{SP}$. Therefore, in cases where the differentiation value I' is measured successively with the passage of time, the alteration of the refractive index of the metal film 12 and the alteration of the refractive index of the sensing substance 30, which is in contact with the metal film 12, are capable of being detected.

In particular, in this embodiment, in cases where the test body contained in the liquid sample 11 is a specific substance, which is capable of undergoing the binding with the sensing substance 30, the refractive index of the sensing substance 30 alters in accordance with the state of the binding of the sensing substance 30 and the test body with each other. Therefore, in cases where the differentiation value I' described above is measured successively, detection is capable of being made as to whether the test body is or is not the specific substance, which is capable of undergoing the binding with the sensing substance 30.

Also, in this embodiment, the metal film 12 has the region 12a, to which the sensing substance 30 has not been fixed, and the region 12b, to which the sensing substance 30 has been fixed, and the reference measurement and the measurement of the state of the binding of the sensing substance 30 and the test body with each other are made simultaneously. Therefore, in cases where the difference between the measured value obtained from the region 12a and the measured value obtained from the region 12b is calculated, the measurement result canceling a measurement error, which occurs due to adverse effects of an alteration of the temperature of the liquid sample 11, and the like, is capable of being obtained.

In this embodiment, by way of example, the metal film 12 is employed as the reference measurement surface. The reference measurement surface should preferably be free from the characteristics of undergoing the binding with the liquid sample 11, which is the substance to be analyzed. By way of example, a reference measurement surface, to which an alkyl thiol has been fixed, may be employed. Also, an antibody acting as the sensing substance may be fixed to the measurement surface for the test body.

The embodiment described above is not limited to the use for the reference measurement and the measurement of the state of the binding of the sensing substance 30 and the test body with each other. Also, for a certain kind of analysis, instead of the liquid sample 11 being supplied continuously into the measurement flow path 55 at the time of the measurement, the operation of the pump 62 may be ceased after the measurement flow path 55 has been filled with the liquid sample 11. Further, after the measurement has been made, the pump 62 may again be actuated. In this manner, the flow of the liquid sample 11 may be ceased at the time of the measurement. In such cases, adverse effects of noise due to the occurrence of vibrations, and the like, are capable of being suppressed. Therefore, the measurement accuracy is capable of being enhanced.

Figure 7A:
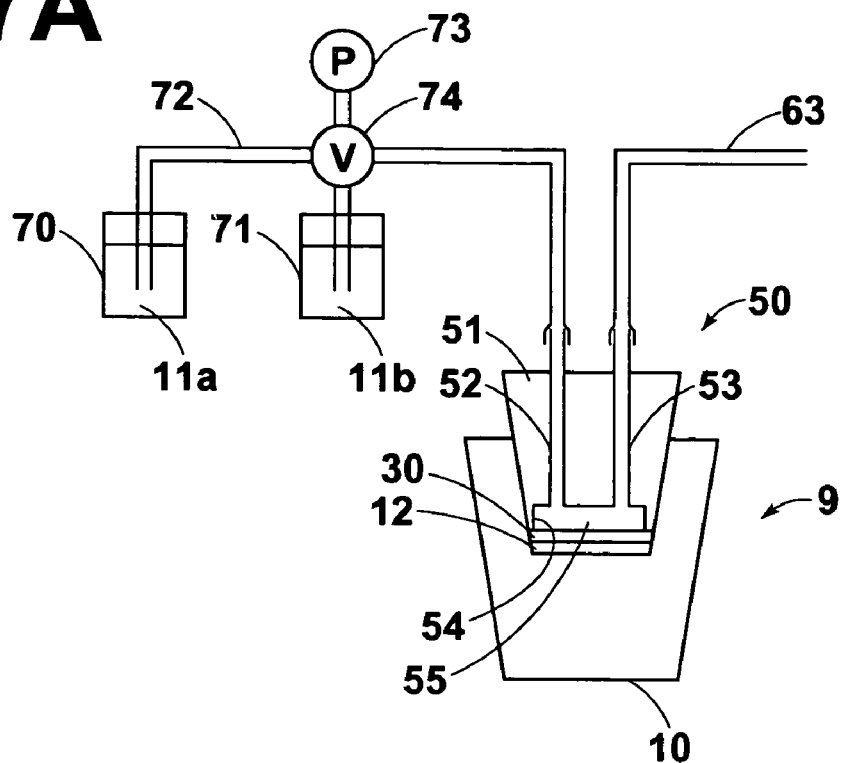
FIG. 7A is a side view showing a different example of how a sample is supplied in the surface plasmon sensor of FIG. 1.

FIG. 7A is a side view showing a different example of how a sample is supplied in the surface plasmon sensor 1 of FIG. 1. In the example illustrated in FIG. 7A, two liquid reservoirs 70 and 71 are prepared. Also, the connection of the supply path is changed over with a valve 74. In this manner, the kind of the liquid sample supplied to the flow path unit 50 is changed over between a liquid sample 11a and a liquid sample 11b. In FIG. 7A, reference numeral 72 represents a pipe, and reference numeral 73 represents a pump.

Figure 7B:
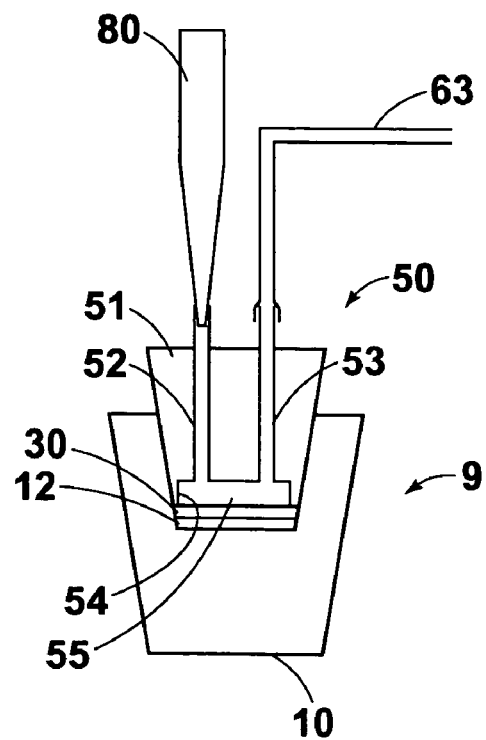
FIG. 7B is a side view showing a further different example of how a sample is supplied in the surface plasmon sensor of FIG. 1.

FIG. 7B is a side view showing a further different example of how a sample is supplied in the surface plasmon sensor 1 of FIG. 1. In the example illustrated in FIG. 7B, in lieu of the liquid sample being supplied from the liquid reservoir by use of the pump, the liquid sample may be supplied into the measurement flow path 55 by use of a disposable type of pipette 80.

Also, as a different example of a modification of the embodiment described above, the sealing section 54 may not be formed at the bottom part of the flow path holder 51. Further, the flow path unit 50 may be loaded into the analysis chip 9, such that the bottom surface of the flow path holder 51 may not come into contact with the combination of the metal film 12 and the sensing substance 30. In this manner, the space formed between the bottom surface of the flow path holder 51 and the combination of the metal film 12 and the sensing substance 30 may be utilized as the measurement flow path.

Further, in cases where a plurality of kinds of liquid samples are changed over with one another, air bubbles having a size identical with the inside diameter of the supply path 52 may be mixed into the supply path 52. In such cases, the problems are capable of being prevented from occurring in that the liquid sample having been supplied most recently and the liquid sample to be supplied subsequently mix with each other. In order for the air bubbles to be mixed into the supply path 52, air may be sucked into the pipette or the pump and may thus be supplied into the supply path 52.

A measuring system in a second embodiment of the analysis apparatus in accordance with the present invention, which second embodiment is constituted as a leaky mode sensor, will be described hereinbelow with reference to FIG. 8. In FIG. 8, similar elements are numbered with the same reference numerals with respect to FIG. 3.

The second embodiment of the analysis apparatus in accordance with the present invention is constituted as the leaky mode sensor through modification of the aforesaid first embodiment constituted as the surface plasmon sensor. In the second embodiment, an analysis chip 109 provided with the dielectric material block 10 is employed. A cladding layer 40 is formed on one surface of the dielectric material block 10 (i.e., the top surface of the dielectric material block 10 in FIG. 8). Also, an optical waveguide layer 41 is formed on the cladding layer 40.

By way of example, the dielectric material block 10 is made from a synthetic resin or optical glass, such as BK7. The cladding layer 40 is formed in a thin film-like shape by use of a dielectric material having a refractive index lower than the refractive index of the dielectric material block 10, or a metal, such as gold. The optical waveguide layer 41 is formed in a thin film-like shape by use of a dielectric material, such as PMMA, having a refractive index higher than the refractive index of the cladding layer 40. In cases where the cladding layer 40 is constituted of a thin gold film, the film thickness of the cladding layer 40 may be approximately 36.5 nm. In cases where the optical waveguide layer 41 is constituted of PMMA, the film thickness of the optical waveguide layer 41 may be approximately 700 nm.

With the leaky mode sensor having the constitution described above, in cases where the laser beam 13 having been produced by the laser beam source 14 passes through the dielectric material block 10 and impinges upon the cladding layer 40 at an incidence angle, which is not smaller than the total reflection angle, the laser beam 13 is totally reflected from each of the interface 11a and the interface 10b between the dielectric material block 10 and the cladding layer 40. However, the light of a specific wave number, which has passed through the cladding layer 40 and has impinged upon the optical waveguide layer 41 at a specific incidence angle, is propagated in a guided mode through the optical waveguide layer 41. In cases where the guided mode is thus excited, the majority of the incident light is taken into the optical waveguide layer 41. Therefore, the intensity of the light, which has been totally reflected from each of the interface 10a and the interface 10b, becomes markedly low, and the attenuated total reflection thus occurs.

The wave number of the guided optical wave in the optical waveguide layer 41 depends upon the refractive index of the sensing substance 30, which is located on the optical waveguide layer 41. Therefore, in cases where the aforesaid specific incidence angle, which is associated with the occurrence of the attenuated total reflection, is detected, the refractive index of the sensing substance 30 is capable of being analyzed. Also, in accordance with the differentiation value I' outputted by each of the differential amplifiers 18a, 18b, 18c, . . . of the differential amplifier array 18, an alteration of the state of the binding of the sensing substance 30 and the test body contained in the liquid sample 11 is capable of being analyzed.

With the second embodiment, the same effects as those with the first embodiment described above are capable of being obtained.

Figure 9:
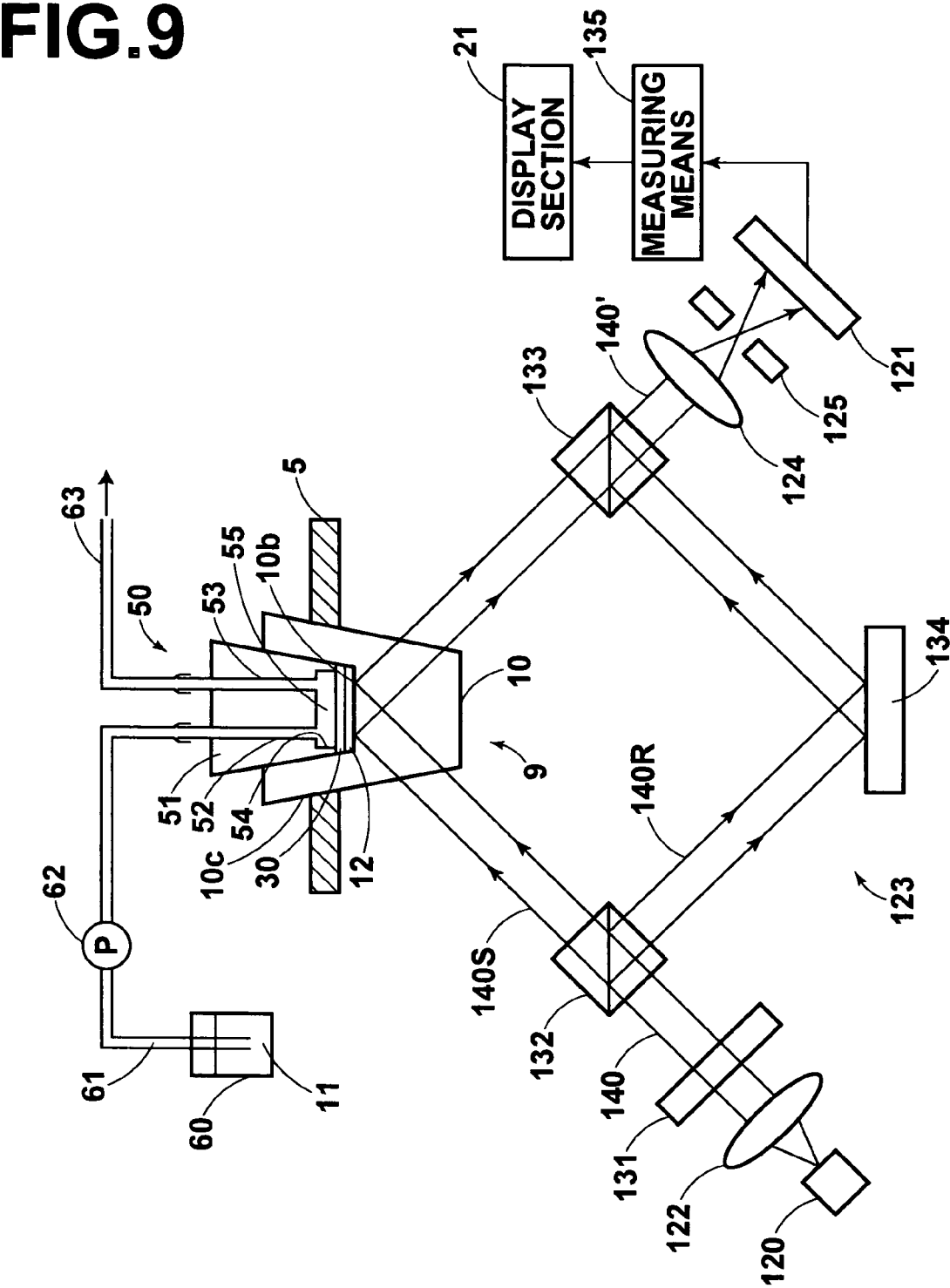
FIG. 9 is a side view showing a measuring system in a third embodiment of the analysis apparatus in accordance with the present invention, which third embodiment is constituted as a surface plasmon sensor.

A measuring system in a third embodiment of the analysis apparatus in accordance with the present invention, which third embodiment is constituted as a surface plasmon sensor, will be described hereinbelow with reference to FIG. 9. In FIG. 9, similar elements are numbered with the same reference numerals with respect to FIG. 3. The surface plasmon sensor of the third embodiment is constituted basically in the same manner as that for the surface plasmon sensor of the first embodiment, except for how measurement are made.

FIG. 9 is a side view showing the measuring system in the third embodiment of the analysis apparatus in accordance with the present invention, which third embodiment is constituted as the surface plasmon sensor. As illustrated in FIG. 9, a laser beam source 120 and a CCD image sensor 121 are located at the position for measurement in the surface plasmon sensor. A collimator lens 122, an interference optical system 123, a converging lens 124, and an aperture member 125 are located between the laser beam source 120 and the CCD image sensor 121. The combination of the laser beam source 120, the CCD image sensor 121, the collimator lens 122, the interference optical system 123, the converging lens 124, and the aperture member 125, and the same combination of the laser beam source 120, the CCD image sensor 121, the collimator lens 122, the interference optical system 123, the converging lens 124, and the aperture member 125 are located such that measurements are capable of being made in a parallel manner with respect to the interface 10$a$ and the interface 10$b$ of the analysis chip 9.

The interference optical system 123 comprises a polarizing filter 131, a semi-transparent mirror 132, a semi-transparent mirror 133, and a mirror 134. The CCD image sensor 121 is connected to measuring means 135. The measuring means 135 is connected to the display section 21.

How analyses are made with the surface plasmon sensor of the third embodiment will be described hereinbelow.

The laser beam source 120 is actuated, and a laser beam 140 is radiated out in the state of divergent light from the laser beam source 120. The laser beam 140, which has been radiated out from the laser beam source 120, is collimated by the collimator lens 122, and the collimated laser beam 140 impinges upon the polarizing filter 131. The collimated laser beam 140 is polarized by the polarizing filter 131, such that the laser beam 140 impinges as the P-polarized light upon the interface 10$a$ and (or the interface 10$b$). The laser beam 140 is then split by the semi-transparent mirror 132 into a reference laser beam 140R and a laser beam 140S. The laser beam 140S, which has passed through the semi-transparent mirror 132, impinges upon the interface 10$a$ (or the interface 10$b$). The laser beam 140S, which has been totally reflected from the interface 10$a$ (or the interface 10$b$), and the reference laser beam 140R, which has been reflected from the mirror 134, impinge upon the semi-transparent mirror 133 and are thus combined with each other into a combined laser beam 140' by the semi-transparent mirror 133. The combined laser beam 140' is converged by the converging lens 124 and passes through an aperture of the aperture member 125. The combined laser beam 140', which has passed through the aperture of the aperture member 125, is detected by the CCD image sensor 121. With the combined laser beam 140' detected by the CCD image sensor 121, interference fringes occur in accordance with the state of the interference of the laser beam 140S and the reference laser beam 140R with each other.

After the liquid sample 11 has been supplied into the analysis chip 9, the measurements may be made successively. Also, an alteration of the interference fringes detected by the CCD image sensor 121 may be detected. In this manner, a judgment is capable of being made as to whether the test body contained in the liquid sample 11 undergoes or does not undergo the binding with the sensing substance 30, which has been fixed to the surface of the metal film 12.

Specifically, the refractive index of the sensing substance 30 alters in accordance with the state of the binding of the test body, which is contained in the liquid sample 11, and the sensing substance 30 with each other. 18Therefore, the state of the interference alters at the time at which the laser beam 140S, which has been totally reflected from the interface 10$a$ (or the interface 10$b$), and the reference laser beam 140R are combined with each other by the semi-transparent mirror 133. Accordingly, the detection as to whether the binding has or has not occurred is capable of being made in accordance with the alteration of the interference fringes. In accordance with the principle described above, the measuring means 135 makes the detection as to whether the binding has or has not occurred. The result of the detection is displayed on the display section 21.

With the third embodiment described above, the same effects as those with the first embodiment are capable of being obtained.

Figure 10:
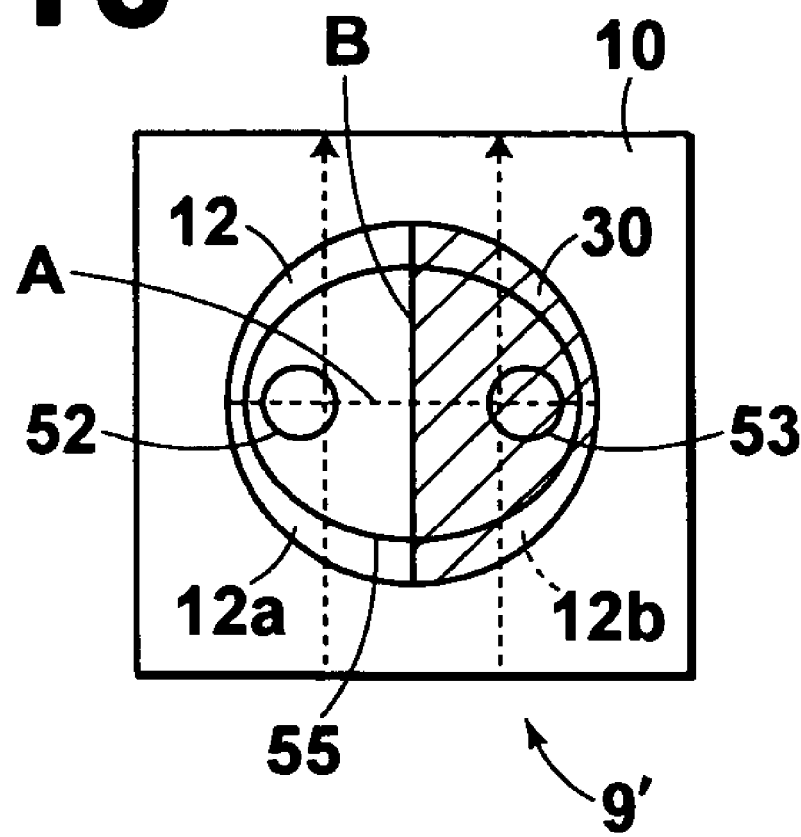
FIG. 10 is a plan view showing a different example of a liquid sample flow path within an analysis chip.

Each of the first, second, and third embodiments described above may be modified such that, as in the cases of an analysis chip 9' illustrated in FIG. 10, the two regions 12$a$ and 12$b$ of the metal film 12 have axisymmetric shapes formed with a perpendicular bisector B of the straight line A, which connects the center point of the outlet of the supply path 52 and the center point of the inlet of the discharging path 53 with each other, being taken as an axis of symmetry. In such cases, the advantages concerning the constitution of the analysis apparatus are capable of being obtained in that the spacing between the laser beam, which is irradiated to the region 12$a$, and the laser beam, which is irradiated to the region 12$b$, is capable of being kept wide.

Also, in cases where the analyses are made by use of the analysis chip 9' illustrated in FIG. 10, the air bubbles having a size identical with the inside diameter of the supply path 52 may be mixed into the supply path 52 as described above. Further, at the time of the measurement, the flow of the liquid sample 11 may be ceased. In this manner, in cases where nonuniformity occurs with the distribution of the concentration of the liquid sample 11 within the measurement flow path 55, the distribution of the concentration of the liquid sample 11 within the measurement flow path 55 is capable of being rendered uniform, while the flow of the liquid sample 11 is being ceased. Therefore, accurate analyses are capable of being made.

What is claimed is:

1. An analysis method, comprising the steps of:
   i) preparing a well-shaped analysis chip, which is provided with a dielectric material block transparent with respect to a light beam having been produced by a light source, a thin film layer formed on one surface of the dielectric material block, and a sample support section capable of supporting a sample on a surface of the thin film layer, the thin film layer being provided with two different regions, which have different characteristics, on the surface of the thin film layer,
   ii) releasably loading a flow path unit into the well-shaped analysis chip, the flow path unit being provided with a supply path, through which the sample is supplied onto the surface of the thin film layer, and a discharging path, through which the sample is discharged from the surface of the thin film layer,
   iii) irradiating the light beam, which has been produced by the light source, to each of a first interface, which is an interface between one of the two different regions of the thin film layer and the dielectric material block, and a second interface, which is an interface between the other region of the thin film layer and the dielectric material block, substantially simultaneously in a parallel manner and at an incidence angle such that a total reflection condition is obtained at each of the first interface and the second interface,
   iv) detecting each of an intensity of the light beam, which has been totally reflected from the first interface, and an intensity of the light beam, which has been totally reflected from the second interface, with independent detecting operations,
   v) acquiring refractive index information with regard to a substance to be analyzed, which is located on the thin film layer, in accordance with results of the detection of the light beam intensities, and
   vi) performing at least one of storing the acquired refractive index information in a memory, displaying the acquired refractive index information on a display, outputting the acquired refractive index information to a printing device and transmitting the acquired refractive index information to a processor.

2. An analysis method as defined in claim 1 wherein either one of the two different regions of the thin film layer is a reference signal measuring region, which is free from characteristics of undergoing reaction with the sample.

3. An analysis method as defined in claim 2 wherein the two different regions of the thin film layer have axisymmetric shapes formed with a straight line, which connects a center point of an outlet of the supply path and a center point of an inlet of the discharging path with each other, being taken as an axis of symmetry.

4. An analysis method as defined in claim 2 wherein the two different regions of the thin film layer have axisymmetric shapes formed with a perpendicular bisector of a straight line, which connects a center point of an outlet of the supply path and a center point of an inlet of the discharging path with each other, being taken as an axis of symmetry.

5. An analysis method as defined in claim 1 wherein the two different regions of the thin film layer have axisymmetric shapes formed with a straight line, which connects a center point of an outlet of the supply path and a center point of an inlet of the discharging path with each other, being taken as an axis of symmetry.

6. An analysis method as defined in claim 1 wherein the two different regions of the thin film layer have axisymmetric shapes formed with a perpendicular bisector of a straight line, which connects a center point of an outlet of the supply path and a center point of an inlet of the discharging path with each other, being taken as an axis of symmetry.

7. An analysis method as defined in claim 1 wherein the detection of each of the intensity of the light beam, which has been totally reflected from the first interface, and the intensity of the light beam, which has been totally reflected from the second interface, is performed while the supply of the sample to the flow path unit is being ceased.

8. An analysis method as defined in claim 1 wherein the different characteristics of the two different region comprise providing a sensing substance on only one of the two different regions of the thin film layer such that the sensing substance binds with the substance to be analyzed, and the refractive index information alters in accordance with the state of the binding of the sensing substance and the substance to be analyzed.

9. An analysis method as defined in claim 1 wherein the sample supplied onto the surface of the thin film layer is a single type of liquid to be analyzed.

10. An analysis apparatus, comprising:
i) a light source for producing a light beam,
ii) a well-shaped analysis chip, which is provided with a dielectric material block transparent with respect to the light beam having been produced by the light source, a thin film layer formed on one surface of the dielectric material block, and a sample support section capable of supporting a sample on a surface of the thin film layer, the thin film layer being provided with two different regions, which have different characteristics, on the surface of the thin film layer,
iii) a flow path unit, which is releasably loaded into the well-shaped analysis chip, the flow path unit being provided with a supply path, through which the sample is supplied onto the surface of the thin film layer, and a discharging path, through which the sample is discharged from the surface of the thin film layer,
iv) an optical system for irradiating the light beam, which has been produced by the light source, to each of a first interface, which is an interface between one of the two different regions of the thin film layer and the dielectric material block, and a second interface, which is an interface between the other region of the thin film layer and the dielectric material block, substantially simultaneously in a parallel manner and at an incidence angle such that a total reflection condition is obtained at each of the first interface and the second interface,
v) photo detecting means for detecting each of an intensity of the light beam, which has been totally reflected from the first interface, and an intensity of the light beam, which has been totally reflected from the second interface, with independent detecting operations, and
vi) refractive index information acquiring means for acquiring refractive index information with regard to a substance to be analyzed, which is located on the thin film layer, in accordance with results of the detection of the light beam intensities, which detection has been made by the photo detecting means.

11. An analysis apparatus as defined in claim 10 wherein either one of the two different regions of the thin film layer is a reference signal measuring region, which is free from characteristics of undergoing reaction with the sample.

12. An analysis apparatus as defined in claim 11 wherein the two different regions of the thin film layer have axisymmetric shapes formed with a straight line, which connects a center point of an outlet of the supply path and a center point of an inlet of the discharging path with each other, being taken as an axis of symmetry.

13. An analysis apparatus as defined in claim 11 wherein the two different regions of the thin film layer have axisymmetric shapes formed with a perpendicular bisector of a straight line, which connects a center point of an outlet of the supply path and a center point of an inlet of the discharging path with each other, being taken as an axis of symmetry.

14. An analysis apparatus as defined in claim 10 wherein the two different regions of the thin film layer have axisymmetric shapes formed with a straight line, which connects a center point of an outlet of the supply path and a center point of an inlet of the discharging path with each other, being taken as an axis of symmetry.

15. An analysis apparatus as defined in claim 10 wherein the two different regions of the thin film layer have axisymmetric shapes formed with a perpendicular bisector of a straight line, which connects a center point of an outlet of the supply path and a center point of an inlet of the discharging path with each other, being taken as an axis of symmetry.

16. An analysis apparatus as defined in claim 10 wherein the photo detecting means performs the detection of each of the intensity of the light beam, which has been totally reflected from the first interface, and the intensity of the light beam, which has been totally reflected from the second interface, while the supply of the sample to the flow path unit is being ceased.

17. An analysis apparatus as defined in claim 10 wherein the different characteristics of the two different regions comprise providing a sensing substance on only one of the two different regions of the thin film layer such that the sensing substance binds with the substance to be analyzed, and the refractive index information alters in accordance with the state of the binding of the sensing substance and the substance to be analyzed.

* * * * *